United States Patent [19]
Okuda et al.

[11] Patent Number: 5,629,338
[45] Date of Patent: May 13, 1997

[54] TANNINS AND LIPASE INHIBITORS CONTAINING THE SAME AS ACTIVE INGREDIENTS

[75] Inventors: Takuo Okuda; Takashi Yoshida; Tsutomu Hatano; Toshitaka Hashimoto; Akiko Yamashita, all of Okayama; Susumu Shimura, Saitama; Yoshio Itoh, Tokyo, all of Japan

[73] Assignee: Lotte Co., Ltd., Tokyo, Japan

[21] Appl. No.: 608,815

[22] Filed: Feb. 29, 1996

[30] Foreign Application Priority Data

Mar. 24, 1995 [JP] Japan ................................. 7-66612

[51] Int. Cl.⁶ ........................ A61K 31/35; C07D 311/60
[52] U.S. Cl. ................................... 514/451; 549/406
[58] Field of Search .......................... 514/451; 549/406

[56] References Cited

FOREIGN PATENT DOCUMENTS 07061981  3/1995  Japan .

OTHER PUBLICATIONS

Kitanaka, S. et al., *Phytochemistry*, 31(8), 1992, pp. 2927–2929.
Kitanaka, S. et al, *J. Nat. Prod.*, 48(5), 1985, p. 849.

*Primary Examiner*—Jacqueline Haley
*Attorney, Agent, or Firm*—Young & Thompson

[57] ABSTRACT

There are disclosed novel tannins, lipase inhibitors containing the same as active constituent and a method for producing the same, wherein said tannins have the formula:

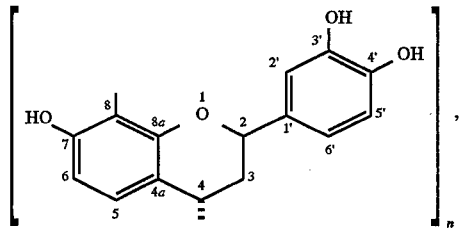

wherein n is 2 or an integer more than 2.

3 Claims, 1 Drawing Sheet

TANNINS AND LIPASE INHIBITORS CONTAINING THE SAME AS ACTIVE INGREDIENTS

BACKGROUND OF THE INVENTION

1. Field of the Invention

The present invention relates to novel tannins and lipase inhibitors containing the same as effective ingredients.

2. Description of the Prior Art

Hitherto, an obesity has been shown to closely relate with diabetes, arteriosclerosis, hypertension and other adult diseases, and has become serious social problem in advanced nations. Obesity is usually caused by an excessive uptake of calories. Restriction of the intake of food would, however, likely cause excessive stress with practical difficulty in restriction.

Fat (triglyceride) is of the highest in calorie, among the food composition and an excess ingestion of fat directly causes obesity. Since fat is degraded by pancreatic lipase for absorption through the small intestine, several efforts have been devoted to develop medicines which inhibit an activity of pancreatic lipase to reduce or prevent obesity.

There are disclosed, for example, agents for anti-obesity and triglyceride reduction comprising polyethers in the Japanese Laid-open Patent Application No. 55-98114, and use of oxetanones in the Japanese Laid-open Patent Application No. 61-152663. Further, diethyl-p-nitrophenylphosphate and tetrahydrolipstatin working as lipase inhibitors have been reported by Biochem. Biophys. Acta., 276, 162 (1972) and Biochem. J., 256, 357 (1988), respectively.

It is also reported that certain food components and crude drug components may inhibit lipase activity, for example, extracts of fruits or the like [Bull. Facul. Agric. Meiji Univ., 69, 15 (1985)], soybean proteins [Agric. Biol. Chem., 37, 1225 (1973)], cereal proteins [Nutrition reports International, 32, 1107 (1985)], and radish seed proteins [Journal of Japanese Food Industry Society, 35, 430 (1980)]. Further, hemicellulose [J. Food Sci., 49, 956 (1984)], wheat bran [Am. j. Clin. Nutr., 42, 629 (1985)] and phosphatidylcholine from radish seed [Bull. Facul. Agric. Meiji Univ., 73, 9 (1986)] have been reported to have inhibitory effects against lipase activity. Furthermore, the Japanese Laid-open Patent Application No. 1-102022 discloses lipase inhibitors consisting of specific components of oolong tea, the Japanese Laid-open Patent Application No. 3-219872 discloses lipase inhibitors consisting of water extracts from green peppers, pumpkins, champignons, *Grifola frondosa*, *Hizikia fusiformis*, green tea, red tea and/or oolong tea, and the Japanese Laid-open Patent Publication No. 3-228664 discloses food for inhibiting lipid absorption in combination with a principal component of green tea, epigallocatechin gallate.

As to tannins, meanwhile, it is known that those from feed plants inhibit lipase, amylase and protease activities [British J. Nutrition, 60,275 (1988)], and that extracts (tannins) from Fiel bean inhibit lipase activity [J. Sci. Food Agric., 30, 458 (1979)]. Further, galloyl quinic acid of the Japanese Patent Publication No. 60-50778, 3'-o-galloyldelphinidin B-2 of the Japanese Patent Publication No. 60-11912 and 4'-6'-galloylsalidroside of the Japanese Patent Publication No. 63-53993 have been published as novel tannins having effects of reducing activities of enzyme proteins in binding therewith, which are useful as metabolism controlling agents.

Furthermore, the Japanese Laid-open Patent Application No. 5-255100 discloses lipase inhibitors of extracts from crude drags, i.e., Angelicae pubscentis Radix, Galanga Rhizoma, Myricae Cortex, Nomame Herba and Cassia Semen, wherein Nomame Herba is a dried above-ground portion of *Cassia nomame* (=*Cassia nomame* Honda=*Cassia mimosoides* L. var. nomame Makino), and the inventors of the present application have uncovered that *Cassia nomame* contains two novel tannins (flavancatechin dimers) and then applied for patents of use as an agent for metabolism improvement under the Japanese Patent Application No. 5-210068 and of a flavonoid lipase inhibitor under the Japanese Patent Application No. 5-210067. These novel flavan-catechin dimers, however, could not achieve sufficient inhibitory effects against lipases.

SUMMARY OF THE INVENTION

It is, therefore, an object of the present invention to provide tannins having surprisingly high activities as lipase inhibitors. Namely, the tannins of the present invention may effectively inhibit lipase activity. The inhibitory effects of the tannins are eleven or more times as strong as that of the crude extract from *Cassia nomame* disclosed in the Japanese Laid-open Patent Publication No. 5-255100.

The tannins according to the present invention are not the compounds of chemically synthesized but of naturally contained in the plant, *Cassia nomame*, decoctions of which have been exercised since long time before. The tannins, therefore, have a high biological safety.

The tannins according to the present invention may be used for preventing obesity and reducing the degree of obesity by virtue of their properties inhibiting digestion and absorption of oils and fat. The tannins of the present invention may also be used for treatment of diseases caused by lipase and for preventing and protecting foods from degradation and stinking.

PREFERRED EMBODIMENTS OF THE INVENTION

Figure 1:
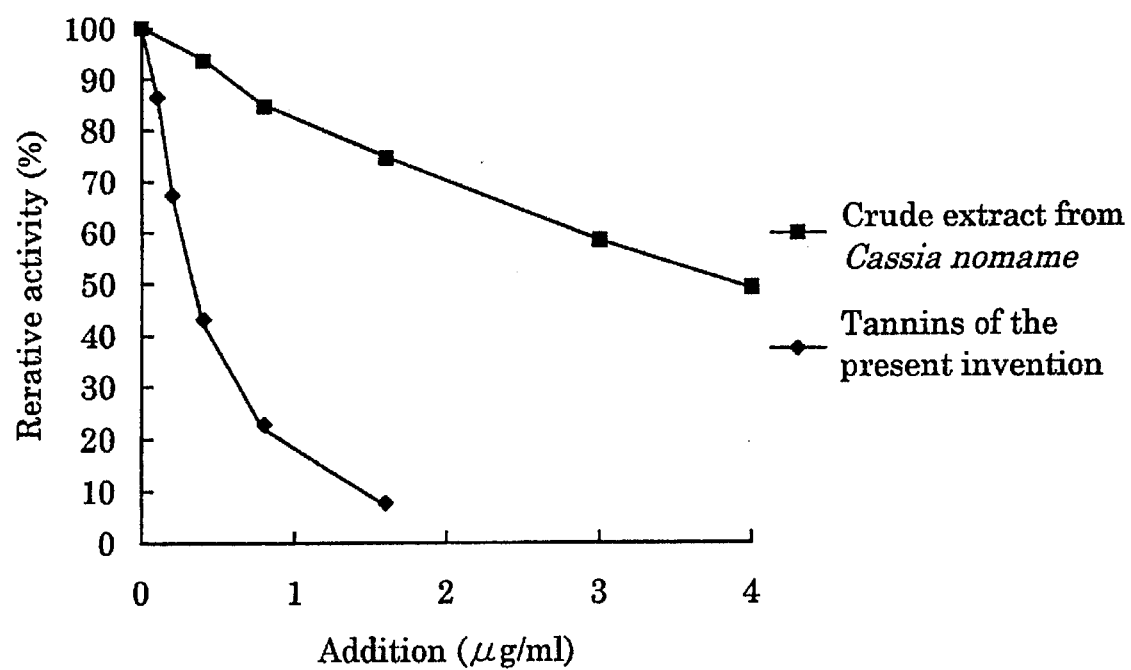
FIG. 1 is a characteristic diagram showing inhibitory effects of tannins according to the present invention and of crude extract from *Cassia nomame* against lipases.

As a result of earnest studies on the components having lipase inhibitory activity in *Cassia nomame*, the present inventors have found that novel tannins of the formula;

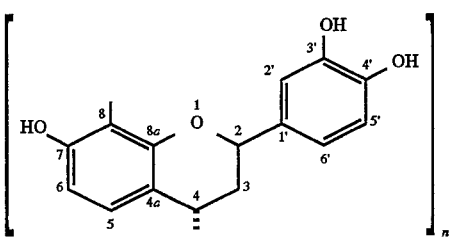

(n is 2 or an integer more than 2)

are available for the purposes of the present invention.

The tannins of the present invention are novel chemical compounds contained in a kind of senna of *Cassia nomame*, which belongs to the leguminous plant. Such compounds, however, are not specifically contained only in *Cassia nomame*, but may be extracted from plants belonging to Acacia species and may also be obtained by chemical synthesis.

There are several methods for extracting the tannins of the present invention from *Cassia nomame*. In a typical method, legumina and leaves, preferably legumina of *Cassia nomame* are treated for extraction with a ketonic solvent such as acetone, and then the extract is further treated for extraction with an ethereal solvent and the resultant extract is purified by a column chromatography.

There may be included as the ketonic extracting solvent other than acetone, for example, aliphatic saturated ketones such as ethyhnethylketone, methylpropyl-ketone and butylmethylketone, unsaturated ketones such as methylvinylketone and methylheptenone, alicyclic ketones such as cyclohexanone and cyclopentanone, aromatic ketones such as acetophenone and benzophenone, and heterocyclic ketones such as acetothienone. These solvents may be used as they are or as being water solution or alcohol solution when need.

On the other hand, the ethereal solvent to be used for the extraction may include aliphatic simple ethers such as ethylether, propylether and butylether, aliphatic mixed ethers such as methylethylether and methylpropylether, aliphatic unsaturated ethers such as vinylether and allylether, aromatic ether such as anisole and phenylbenzylether, and cyclic ether such as ethylene oxide and tetrahydrofuran.

The tannins of the present invention thus obtained are brown powder from the proanthocyanidin fraction, having a number mean molecular weight of 1,020 and a weight mean molecular weight of 1,120. Such tannins are unpublished and novel polymers formed by polymerization of two or more monomers as being represented by the formula described in the above, but the upper limit of polymerization degree is not specified.

The tannins according to the present invention have surprising inhibitory effects against lipase activity and may be used alone or in combination with one or more other lipase inhibitors. Further, those tannins may be used as being diluted with proper solvents, prepared into paste, powder, tablet or granule formulation, or previously mixed in foods.

Additionally, besides for inhibiting lipase activity, the tannins of the present invention may also be used for other purpose of, for instance, tanning leather and the like.

Followings are examples for illustrating the present invention in detail, not for limiting the scope of the present invention.

EXAMPLES

Example 1

Isolation and characterization of tannins of the present invention.

A hundred grams of legumina of *Cassia nomame* were treated for extraction with 70% acetone solution. Acetone was removed by reducing the pressure before the extract was treated with ethylether to obtain 4.1 g of ether-extract. Three point eight grams of the resultant ether-extract were loaded on a TOYOPEARL HW40 column ($\phi$2.2×40 cm) and then eluted with 70% ethanol to collect 256 mg of fractionated extract showing characteristics described below.

The final extract was brown powder, the acetilide of which had a number mean molecular weight of 1,020 and a weight mean molecular weight of 1,120 (GPC). The dominant component consisted of 4 monomers. The light-red color was presented in the reaction of hydrochloric-acidified vanillin method [J. Sci. Food Agric., 29, 788–794 (1978)] and no hexose was detected by anthrone-sulfuric acid method. Analysis of $^{13}$C-NMR spectrum resulted in tannins with ingredient monomer of which of 3', 4', 7-trihydroxyflavan having the formula described below.

$^{13}$C-NMR (acetone-$d_6$+$D_2O$): $\delta$31–35(C-4), 35–38(C-3), 75–80(C-2), 102–110(C-6,8), 113–115(C-2'), 115–117(C-5'), 117–120(C-6', 4a), 128–132(C-5), 133–135(C-1'), 144–146(C-3', 4'), 151–157(C-7, 8a)

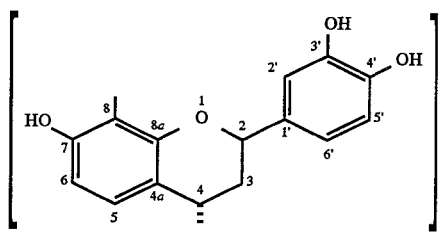

(n is 2 or an integer more than 2)

Example 2

Assay method for lipase activity and evaluation of inhibitory effect against lipase Lipase activity was determined by measuring fluorescence of 4-methylumbelliferone produced in the reaction with oleate ester of 4-methylumbelliferone (4-MUO) which is a substrate of lipase.

4-MUO (substrate) emulsion by 100 μl, porcine pancreatic lipase (Sigma) solution by 50 μl and buffer solution by 50 μl were mixed in a small test tube and the reaction took place at 37° C. for 20 minutes on the final condition of 0.05 mM 4-MUO, 2.2 μg of porcine pancreatic lipase and the McIlvaine buffer (pH7.4). 0.1N HCl by 1 ml was added to stop the reaction and 0.1M sodium citrate by 2 ml was added to adjust the pH of the mixture to approximately 4.3. The fluorescence of 4-methylumbelliferone (excitation wavelength 320 nm and fluorescent wavelength 450 nm) produced by the reaction was then measured by a fluorophotometer.

50% tetraohydrofuran (THF) solution of a sample by 5 μl was added to the reaction system to determine an inhibitory effect against lipase. In the control, 50% THF solution without the sample was added for the reaction. The inhibitory effect was indicated by IC$_{50}$(μg/ml), i.e., the amount of sample for inhibiting 50% of the activity of the control.

Example 3

Inhibitory effects by tannins of the present invention

Inhibitory effects against lipase by crude extracts from *Cassia nomame* and by tannins of the present invention were evaluated in accordance with the methods as described in Example 2.

Preparation of the crude extracts from *Cassia nomame* was performed according to the method described in Examples 1 and 2 of the specification of the Japanese Laid-open Patent Application No. 5-255100. Namely, dried plant bodies of *Cassia nomame* were crushed and five times weight of hexane was added for one-day extraction and delipidation. The extracted residue was then dried by aspiration and five times weight of tetrahydrofuran was added for further one-day extraction. The resultant mixture was then filtered and the filtrate was dried by aspiration to obtain a final extract.

The preparation according to Example 1 was subjected to the assay of the tannins of the present invention.

The results of the assays are shown in FIG. 1. $IC_{50}$ of the crude extract from *Cassia nomame* was approximately 3.8 μg/ml. Meanwhile, the tannins of the present invention has provided remarkable inhibitory effect with those $IC_{50}$ being 0.34 μg/ml which is approximately eleven times as strong as that of the crude extract.

What we claim are:

1. Tannins having the formula:

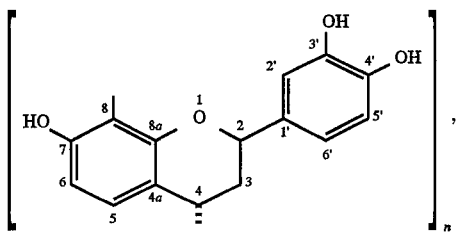

wherein n is 2 or an integer more than 2.

2. Lipase inhibitors containing tannins of the formula:

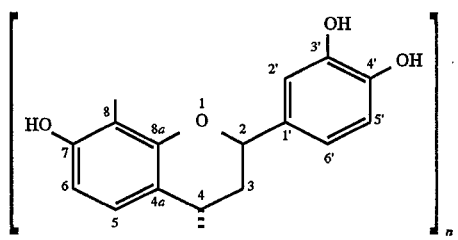

as active ingredients, wherein n is 2 or an integer more than 2.

3. A method for producing tannins of the formula:

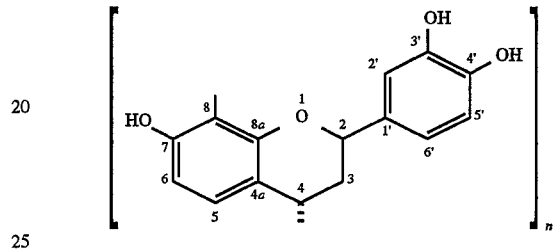

wherein n is 2 or an integral number more than 2 and said method comprises extracting with an ether from an extract obtained by from *Cassia nomame*.

* * * * *